(12) United States Patent
Rakitzis (10) Patent No.: US 8,941,831 B2
(45) Date of Patent: Jan. 27, 2015

(54) INTRA-CAVITY ELLIPSOMETER SYSTEM AND METHOD

(76) Inventor: Theodore Peter Rakitzis, Heraklion-Crete (GR)

( * ) Notice: Subject to any disclaimer, the term of this patent is extended or adjusted under 35 U.S.C. 154(b) by 318 days.

(21) Appl. No.: 13/265,841

(22) PCT Filed: May 4, 2010

(86) PCT No.: PCT/IB2010/001154
§ 371 (c)(1),
(2), (4) Date: Oct. 21, 2011

(87) PCT Pub. No.: WO2010/128395
PCT Pub. Date: Nov. 11, 2010

(65) Prior Publication Data
US 2012/0069336 A1    Mar. 22, 2012

Related U.S. Application Data

(60) Provisional application No. 61/215,322, filed on May 4, 2009.

(51) Int. Cl.
*G01J 4/00* (2006.01)
*G01N 21/21* (2006.01)
*G01N 21/55* (2014.01)

(52) U.S. Cl.
CPC ............ *G01N 21/211* (2013.01); *G01N 21/552* (2013.01); *G01N 2021/212* (2013.01)
USPC .......................................................... 356/369

(58) Field of Classification Search
USPC .......................................................... 356/369
See application file for complete search history.

(56) References Cited

U.S. PATENT DOCUMENTS

| | | | | |
|---|---|---|---|---|
| 5,437,840 A | * | 8/1995 | King et al. | 422/82.08 |
| 5,538,850 A | * | 7/1996 | King et al. | 435/6.12 |
| 5,835,231 A | * | 11/1998 | Pipino | 356/440 |
| 5,943,136 A | * | 8/1999 | Pipino et al. | 356/440 |
| 5,986,768 A | * | 11/1999 | Pipino | 356/440 |
| 6,515,749 B2 | * | 2/2003 | Pipino | 356/440 |
| 7,054,009 B2 | * | 5/2006 | DePue et al. | 356/437 |
| 7,301,639 B1 | * | 11/2007 | Kebabian et al. | 356/437 |
| 7,333,206 B2 | * | 2/2008 | Clark | 356/446 |
| 7,336,359 B1 | * | 2/2008 | Simpson et al. | 356/364 |
| 7,466,409 B2 | * | 12/2008 | Scherer et al. | 356/326 |
| 8,149,411 B2 | * | 4/2012 | Johansen et al. | 356/445 |
| 2005/0094150 A1 | * | 5/2005 | DePue et al. | 356/445 |
| 2005/0225775 A1 | * | 10/2005 | Brunfeld et al. | 356/519 |

* cited by examiner

*Primary Examiner* — Roy M Punnoose
(74) *Attorney, Agent, or Firm* — Booth Udall Fuller, PLC (57) ABSTRACT

A resonant optical cavity ellipsometer system is provided. The system can be used to conduct time-dependent arid sensitive measurement of ellipsometric parameters of matter. In a particular use, the system can provide time resolution of better than 1 microsecond. In a particular implementation, matter can be probed within the evanescent wave generated by intra-cavity total reflection.

26 Claims, 6 Drawing Sheets

INTRA-CAVITY ELLIPSOMETER SYSTEM AND METHOD

CROSS REFERENCE TO RELATED APPLICATIONS

This document claims the benefit of the filing date of U.S. Provisional Patent Application No. 61/215,322, entitled "Intra-Cavity Total Reflection Ellipsometer System for Time-Dependent and Sensitive Measurement of Ellipsometric Parameters of Materials" to Theodore Peter Rakitzis which was filed on May 4, 2009, the disclosure of which is hereby incorporated entirely herein by reference.

BACKGROUND

1. Technical Field

Aspects of this document relate generally to optical systems, and more specifically, to those that measure the ellipsometric parameters of matter within a low-loss optical cavity, including, in some implementations, within the evanescent wave generated by intra-cavity total reflection.

2. Background Art

Ellipsometry is a well-established technique for the non-destructive measurement of characteristics of material systems. The topic is well-described in a number of publications, one such publication being a publication by Collins, titled "Automatic Rotating Element Ellipsometers: Calibration. Operation and Real-Time Applications", Rev. Sci. Instrum. 61(8) (1990). Practice of ellipsometry typically involves causing a spectroscopic beam of electromagnetic radiation, in an imposed, known, state of polarization, to interact with a material system at one or more angle(s) of incidence. Changes in the polarization state of the beam of electromagnetic radiation which occurs as a result of the interaction with the material system gives information about the structure and composition of the material system.

A typical goal in ellipsometry is to measure, for each angle of incidence and wavelength of a beam of electromagnetic radiation caused to interact with a material system, the ellipsometric parameters $\Psi$ and $\delta$ (where $\Psi$ is related to a change in a ratio of magnitudes of orthogonal components $r_p/r_s$ in the beam of electromagnetic radiation, and $\delta$ is the phase shift introduced between the orthogonal components $r_p$ and $r_s$, caused by interaction with the material system:

$$\psi = |r_p/r_s|; \text{ and}$$

$$\delta = (\phi_p - \phi_s).$$

The change of ratio $r_p/r_s$ or the phase shift $\delta$ caused by the interaction of the electromagnetic radiation with the material system can be very small (e.g. $\delta$ can be a value such as 0.001°), so the accurate measurement of $\delta$ using a conventional system requires long data acquisition times for extensive signal averaging, which is sometimes impractical. Further, because of the limited time resolution inherent in conventional methods, fast events, where the value of $\delta$ changes quickly (in relation to the time resolution of the measuring system), cannot be measured by conventional systems and methods.

In cases for which the losses of electromagnetic radiation from interacting with such material systems are small (typically less than 1%), the effect from the interaction with such material system can be amplified by reflecting the radiation repeatedly so as to interact with the material system multiple times (usually at least 100 times). This has been achieved by placing the material system on the reflective surface of an optical cavity, as described in A.C.R. Pipino, "Ultrasensitive Surface Spectroscopy with a Miniature Optical Resonator" Phys. Rev. Lett. 83, 3093 (1999), M. A., Everest et al., "Hemoglobin Adsorption to Silica Monitored with Polarization-Dependent Evanescent-Wave Cavity Ring-Down Spectroscopy", J. Phys. Chem. B 110, 19461 (2006), and U.S. Pat. Nos. 5,986,768 and 5,835,231, the disclosures of which are incorporated herein by this reference. In these cases, methods for the measurement of the losses for the p and s polarization states were described, which allows the determination of $\psi = r_p/r_s$ with much greater sensitivity than single-pass techniques, and allows the determination of $\psi$ on the microsecond timescale, However, these publications fail to provide methods or systems for utilizing multi-pass techniques to measure $\delta$ with increased sensitivity and time-resolution (for example, on the order of the microsecond timescale), Nor is it apparent from the known literature how to do so.

Resonator-enhanced optical inspection systems, and other optical systems, such as those described by U.S. Pat. Nos. 6,653,649, 6,700,840, 6,714,295, 6,717,707, 6,778,307, 7,330,277 B2, the specifications of which are incorporated herein by reference, provide improved resolution, surface detection and other performance improvements in traditional optical systems. However, measurement systems disclosed in the above-referenced U.S. patents are not able to measure the ellipsometric phase angle $\delta$ with a time-resolution of about 1 microsecond or less.

The publication Jacob et al., "Pulsed measurement of high-reflectivity mirror phase retardances", Applied Optics, May 1994, vol. 33, No. 15, pp, 3175-3178, describes methods for the time-dependent measurement of the phase angle $\delta$ upon reflecting light from a high-reflectivity dielectric mirror, However, the measurement system described in this publication is for the characterization of high-reflectivity mirrors, not for the measurement of the ellipsometric parameters of materials. Highly-reflective dielectric mirrors are not ideal as substrates for ellipsometric measurements of materials because all but very careful sample preparation on the mirrors will significantly reduce the reflectivity of the mirrors.

In certain situations, where time resolution is important, no known conventional system cart accurately measure the ellipsometric parameter $\delta$ for some types of material. When the ellipsometric parameter $\delta$ is small, such as, for example, 0.001°, accurately measuring $\delta$ is often problematic or impossible for prior art apparatus and methods. Despite various ellipsometric techniques that have been developed in the past, apparatus and methods have not been developed which can accurately measure the ellipsometric parameter $\delta$ when $\delta$ is small (for example, smaller than about 0.001°) without the necessity for long data acquisition times to allow extensive signal averaging. Long data acquisition times and extensive signal averaging are not always feasible or possible. Further, in some situations the properties of the subject material change quickly. Signal averaging results in relatively poor time resolution. When the properties of the material change faster than the time resolution of an ellipsometric system, such system will not be able to accurately measure the time dependent change in the properties.

The relatively poor time resolution of prior art ellipsometry systems has limited the use of ellipsometry to measurements of the equilibrium or steady-state properties of materials.

SUMMARY

In one aspect, this disclosure provides a device which permits the sensitive time-dependent measurement of the ellipsometric angle $\delta$ of a material system, with time resolution of at least 1 microsecond (for material systems for which the total losses from reflection, absorption, and scattering are small, typically less than 1% per pass of light) with diffraction-limited spatial resolution through utilization of a high-Q (high-quality, low loss) optical cavity, In another aspect, this disclosure includes an ellipsometric system comprising light-generating means for generating at least one first light pulse, first-polarizing means for polarizing at least a portion of such at least one first light pulse into at least one first polarized light pulse, second polarizing means for polarizing at least a portion of such at least one first polarized light pulse into at least one second polarized light pulse and for polarizing at least a portion of such at least one first polarized light pulse into at least one third polarized light pulse, and first-detector means for detecting such at least one second polarized light pulse.

In particular implementations, the ellipsometric system may comprise one or more of the following: Second-detector means for detecting such at least one third polarized light pulse. Evanescent-wave-generating means for generating at least one evanescent wave from at least a portion of such at least one first polarized light pulse. The light-generating means may comprise at least one laser, the evanescent-wave-generating means may comprise at least one closed stable optical cavity, the at least one first-detector means may comprise at least one first photomultiplier, and the at least one second-detector means may comprise at least one second photomultiplier.

In another aspect, this disclosure includes an ellipsometric system comprising at least one light source structured and arranged to generate at least one first light pulse, at least one first-polarizer structured and arranged to polarize at least a portion of such at least one first light pulse into at least one first polarized light pulse, at least one closed stable optical cavity structured and arranged to generate a measurable ellipsometric phase shift in the at least one first polarized light pulse, and at least one first light-detector.

In particular implementations, the ellipsometric system may include one or more of the following: The at least one closed stable optical cavity of the ellipsometric system may be further structured and arranged to generate at least one evanescent wave from at least a portion of the at least one first polarized light pulse. The ellipsometric system may further comprise at least one second-polarizer structured and arranged to polarize at least a portion of such at least one first polarized light pulse into at least one second polarized light pulse and to polarize at least a portion of such at least one first polarized light pulse into at least one third polarized light pulse, and at least one second light-detector structured and arranged to detect such at least one third polarized light pulse, wherein the at least one first light-detector is structured and arranged to detect such at least one second polarized light pulse. The at least one second-polarizer may be structured and arranged so that such at least one third polarized light pulse is substantially orthogonal to such at least one second polarized light pulse. The at least one first-polarizer may be structured and arranged to polarize such at least one first polarized light pulse so that such at least one first polarized light pulse comprises non-zero polarization components both parallel and perpendicular to a first geometric plane. The at least one second-polarizer may be structured and arranged to polarize such at least one first polarized light pulse at an angle about forty-five degrees from such first geometric plane. The at least one first-polarizer and the at least one second-polarizer may be combined in one unitary element.

The light source may comprise at least one laser, the at least one closed stable optical cavity comprises at least one first reflector, and the at least one closed stable optical cavity may comprise at least one second reflector. The at least one closed stable optical cavity may comprise at least one prism, the at least one first reflector may comprise at least one first concave reflecting portion, and the at least one second reflector may comprise at least one second concave reflecting portion. The at least one first light-detector may comprise at least one first photomultiplier, and the at least one second-detector may comprise at least one second photomultiplier. The light source may comprise at least one laser, the at least one closed stable optical cavity may comprise at least one prism, the at least one prism may comprise fused silica, the at least one dosed stable optical cavity may further comprise at least one first reflector, the at least one first reflector may comprise at least one first concave reflecting portion, the at least one closed stable optical cavity may further comprise at least one second reflector, the at least one second reflector may comprise at least one second concave reflecting portion, the at least one first concave reflecting portion may comprise at least one first radius, the at least one second concave reflecting portion may comprise at least one second radius, the at least one first radius may be substantially equal to the at least one second radius, the at least one first light-detector may comprise at least one first photomultiplier, and the at least one second-detector may comprise at least one second photomultiplier.

The at least one closed stable optical cavity may consists essentially of a unitary optical element, the unitary optical element may comprise at least one convex surface, and the unitary optical element may be structured and arranged to provide total internal reflection of such first polarized light pulse, The at least one unitary optical element may comprise at least one first substantially planar surface structured and arranged so that such at least a portion of such at least one first polarized light pulse enters the at least one unitary optical element, and the at least one unitary optical element may comprise at least one second substantially planar surface structured and arranged so that at least a portion of such at least one first polarized light pulse exits the at least one unitary optical element. The at least one first substantially planar surface may comprise at least one first high-reflectivity coating structured and arranged to internally reflect at least 97% of such at least one first polarized light pulse, the at least one second substantially planar surface may comprise at least one second high-reflectivity coating structured and arranged to internally reflect at least 97% of such at least one first polarized light pulse, and the at least one convex surface may comprise a surface roughness less than 10 nm RMS.

The at least one first substantially planar surface may comprise at least one first high-reflectivity coating structured and arranged to internally reflect at least 99.9% of such at least one first polarized light pulse, the at least one second substantially planar surface may comprise at least one second high-reflectivity coating structured and arranged to internally reflect at least 99.9% of such at least one first polarized light pulse, and the at least one convex surface may comprise a surface roughness less than 0.5 nm RMS. The ellipsometric system may further comprise at least one lens structured and arranged to transverse mode match such at least one first polarized light pulse for the at least one closed stable optical cavity. The at least one closed stable optical cavity may comprise at least one substantially regular, substantially planar polygon, At least one input element may be structured and arranged so that at least a portion of such at least one first polarized light pulse enters the at least one closed stable optical cavity. The at least one input element may comprise at least one prism. The at least one input element may allow a portion of such at least one first polarized light pulse to enter the at least one closed stable optical cavity via frustrated total reflection photon tunneling.

The ellipsometric system may further comprise at least one output element structured and arranged so that at least a portion of such at least one first polarized light pulse exits the at least one closed stable optical cavity. The at least one output element may allow a portion of such at least one first polarized light pulse to exit the at least one closed stable optical cavity via frustrated total reflection photon tunneling. The at least one light source may be selected from the group consisting of picosecond pulsed laser, femtosecond pulsed laser, diode laser, pulsed dye laser, and continuous wave laser. The at least one first light-detector may comprise at least one first photodiode, and the at least one second light-detector may comprise at least one second photodiode.

In another aspect, this disclosure includes a method of measuring the ellipsometric angle δ of a test material, the method comprising the steps of: generating at least one first light pulse, polarizing such at least one first light pulse into at least one first polarized light pulse, injecting the at least one first polarized light pulse into at least one closed stable optical cavity so that test material situated to interact with the at least one first polarized light pulse will partially absorb such at least one first polarized light pulse, polarizing at least a portion of such at least one first polarized light pulse, that has exited the at least one closed stable optical cavity, into at least one second polarized light pulse, detecting such at least one second polarized light pulse, and calculating the ellipsometric angle δ of the test material from the detected second polarized light pulse. In particular implementations, the method may comprise injecting the at least one first polarized light pulse so that the first polarized light pulse generates at least one evanescent wave, and interacting the test material with the at least one evanescent wave so that the test material partially absorbs the at least one evanescent wave.

Aspects, implementations, embodiments and applications of the disclosure presented here are described below in the drawings and description. Unless specifically noted, it is intended that the words and phrases in the specification and the claims be given their plain, ordinary, and accustomed meaning to those of ordinary skill in the applicable arts, The inventor is fully aware that be can be his own lexicographers if desired. The inventor expressly elects, as his own lexicographer, to use only the plain and ordinary meaning of terms in the specification and claims unless it is clearly stated otherwise and then further, expressly sets forth the "special" definition of that term and explains how it differs from the plain and ordinary meaning. Absent such clear statements of intent to apply a "special" definition, it is the inventor's intent and desire that the simple, plain and ordinary meaning to the terms be applied to the interpretation of the specification and claims.

The inventor is also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventor is fully informed of the standards and application of the special provisions of 35 U.S.C. §112, ¶6. Thus, the use of the words "function," "means" or "step" in the Description, Drawings or claims is not intended to somehow indicate a desire to invoke the D special provisions of 35 U.S.C. §112, ¶6, to define this disclosure. To the contrary, if the provisions of 35 U.S.C. §112, ¶6 are sought to be invoked to define the disclosure, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventor not to invoke the provisions of 35 U.S.C, §112, ¶6. Moreover, even if the provisions of 35 U.S.C. §112, ¶6 are invoked to define the claimed disclosure, it is intended that the disclosure not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter he described in conjunction with the appended drawings, where like designations denote like elements, and.

DESCRIPTION

This disclosure, its aspects and implementations, are not limited to the specific components or assembly procedures disclosed herein. Many additional components and assembly procedures known in the art consistent with the intended system and/or assembly procedures for an ellipsometer system will become apparent for use with particular implementations from this disclosure. Accordingly, for example, although particular Implementations are disclosed, such implementations and implementing components may comprise any shape, size, style, type, model, version, measurement, concentration, material, quantity, and/or the like as is known in the art for such ellipsometer systems and implementing components, consistent with the intended operation.

It is desirable to improve the capabilities of ellipsometers to include the measurement of the ellipsometric phase angle d with the capability of very fast time-resolution (such as, for example, on the order of 1 microsecond or less), for the measurement of dynamics at surfaces. Examples of dynamics at surfaces include crystal growth, thin film deposition, the detection of biomolecules binding to a surface (optical biosensing), and the measurement of structural changes of biomolecules and polymers at surfaces. For all these examples, the time scale of the physical processes involved is between the millisecond (ms) to nanosecond (ns) time scale, which is too fast for current ellipsometric systems, but can be achieved with the innovation described herein. There has been a long-felt need to measure the time-dependent properties of surfaces, such as, for example, for the purposes described above. The improvement of the time resolution of ellipsometry in the present invention allows the measurement of the time-dependent properties of surfaces.

Figure 1:
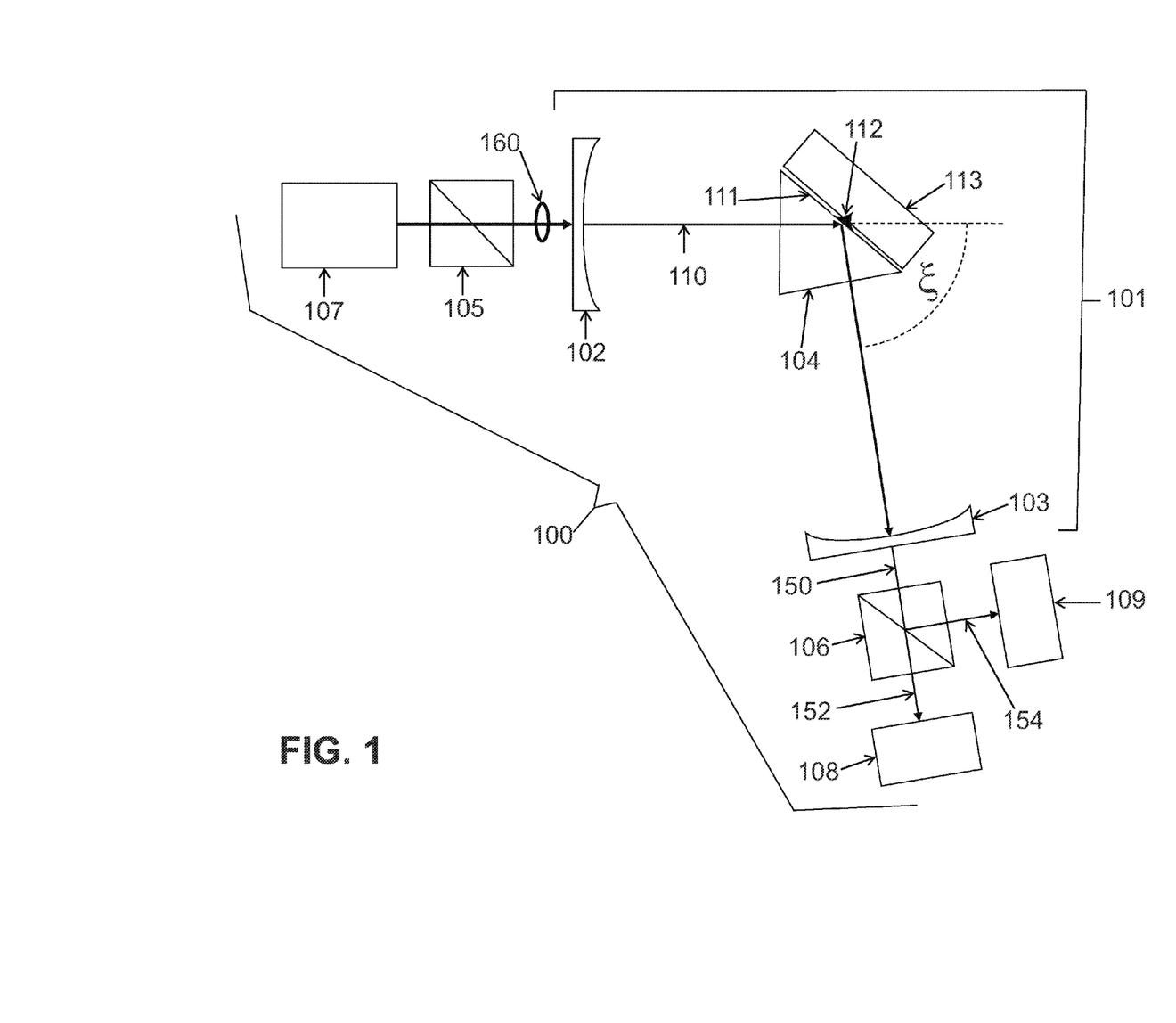
FIG. 1 illustrates a schematic top elevational view of an ellipsometer system in accordance with a particular embodiment.

FIG. 1 illustrates a schematic top elevational view of ellipsometer system 100 in accordance with a first embodiment. Ellipsometer system 100 comprises optical cavity 101. Optical cavity 101 may comprise three elements: reflector 102, reflector 103, and prism 104. In particular implementations, considering issues such as, for example, spatial constraints, tolerances, calibration issues, materials employed, manufacturing costs, maintenance costs, and other factors known to those of ordinary skill in the art, other arrangements may be configured which achieve the functional operation of the presently disclosed systems but which use, for example, a different number of elements, a different element configuration, and/or replacement of a reflector with something functionally similar to a reflector.

In the example provided, reflectors 102 and 103 are highly-reflective. Reflectors 102 and 103, for example, comprise a reflectivity of at least 97%, and preferably at least 99.9%. Reflectors 102 and 103 are concave, as shown, with approximately equal radii or curvature. In particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, a reflectivity less than 97%, non-concave reflectors, and/or reflectors of unequal radii.

Ellipsometer system 100 comprises light source 107, as shown (at least embodying herein a light-generating means for generating at least one laser pulse). Ellipsometer system 100 comprises polarizer 105 (at least embodying herein a first-polarizing means for polarizing at least a portion of such at least one first light pulse into at least one first polarized light pulse). Ellipsometer system 100 comprises polarizer 106. Polarizer 105, for this embodiment, is interposed between light source 107 and reflector 102. In operation, light source 107 generates a radiation pulse 110, Ellipsometer system 100 comprises lens 160 selected to traverse mode match radiation pulse 110 to cavity 101, Radiation pulse 110 passes through lens 160 and polarizer 105 into cavity 101. Polarizer 105 polarizes radiation pulse 110 at an angle $\theta_1$ □(not shown) to the geometric plane formed by reflector 102, reflector 103, and prism 104. Angle $\theta_1$, in particular implementations, is substantially □ 45° so that radiation pulse 110 comprises nonzero polarization components both parallel and perpendicular to such geometric plane. In particular implementations, the initial phase relation of polarization components is fixed. In particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, larger or smaller values for $\theta_1$, multiple light sources, and/or alternate positioning.

Prism 104 deflects radiation pulse 110 by angle ξ toward reflector 103, as shown. Prism 104 provides "total internal reflection" as the term is applied by those of ordinary skill in the art. Prism 104 comprises material with a very high internal transmission (in particular implementations at least 97% over 10 mm, preferably at least 99,9% over 10 mm) of radiation pulse 110. Prism 104 comprises prism surface 120 and prism surface 121. Prism surfaces 120 and 121, individually or collectively may comprise an anti-reflective coating. In particular implementations, one or both of prism surfaces 120 and 121 may comprise a reflectivity of no more than 0.5%, preferably no more than 0.1%. The reflection losses from prism 104, in particular implementations, should be less than the reflection losses from reflector 102 and reflector 103. In particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, prism(s) that comprise material with lower values for internal transmission, and/or prism surfaces with greater reflectivities, During operation, total internal reflection occurs at prism surface 111, creating evanescent wave 112 decaying exponentially into the region external to prism surface 111 (at least embodying herein evanescent-wave-generating means for generating at least one evanescent wave from at least a portion of such at least one first polarized light pulse). Material 113 is placed within the decay length of evanescent wave 112, as shown, Radiation pulse 110 reflects off reflector 103, the majority of radiation pulse 110 is reflected back toward prism 104, and a small portion of radiation pulse 110, transmitted pulse 150, is transmitted through reflector 103 toward polarizer 106, as shown. Polarizer 106 separates transmitted pulse 150 into first polarization component 152 and second polarization component 154, as shown (at least embodying herein second polarizing means for polarizing at least a portion of such at least one first polarized light pulse into at least one second polarized light pulse and for polarizing at least a portion of such at least one first polarized light pulse into at least one third polarized light pulse). Polarizer 106 separates transmitted pulse 150 so that first polarization component 152 is substantially orthogonal to second polarization component 154 and polarizes transmitted pulse 150 at angle $\theta_2$ (not shown) to the geometric plane formed by the first and second polarization components 152 and 154 orthogonal to each other. Angle $\theta_2$ may be substantially 45°. In particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, larger or smaller values for $\theta_2$, an arrangement with first polarization component at an angle larger or smaller than orthogonal to second polarization component, utilizing circularly or elliptically polarized light, and/or alternate positioning.

Ellipsometer system 100 comprises detectors 108 (at least embodying herein first-detector means for detecting such at least one second polarized light pulse) and 109 (at least embodying herein second-detector means for detecting such at least one third polarized light pulse). Detectors 108 and 109 may each comprise a photomultiplier. Detector 10$ is positioned so that a first polarization component 152 is measured and detector 109 is positioned so that second polarization component 154 is measured, as shown. Data collected from detector 108 and detector 109 is used to determine decay time of radiation pulse 110 and to determine time-dependent polarization of the radiation pulse 110. By monitoring the time-dependence of the polarization during the lifetime of the radiation pulse 110, the ellipsometric phase shift can be accurately determined from the oscillation frequency of the polarization. Such decay time and time-dependent polarization are evaluated to determine properties of material 113. In particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, detectors other than photomultipliers, detectors comprising avalanche photodiodes, detectors comprising other photon-counting technologies, alternate positioning, and/or utilizing only one detector instead of two detectors (or more) to determine decay time and/or time-dependent polarization.

In particular implementations, material 113 may be probed by radiation pulse 110 a number of times N, equal to the ratio of the decay time to one-half the round trip time. This value will typically be on the order of 1,000.

Figure 2:
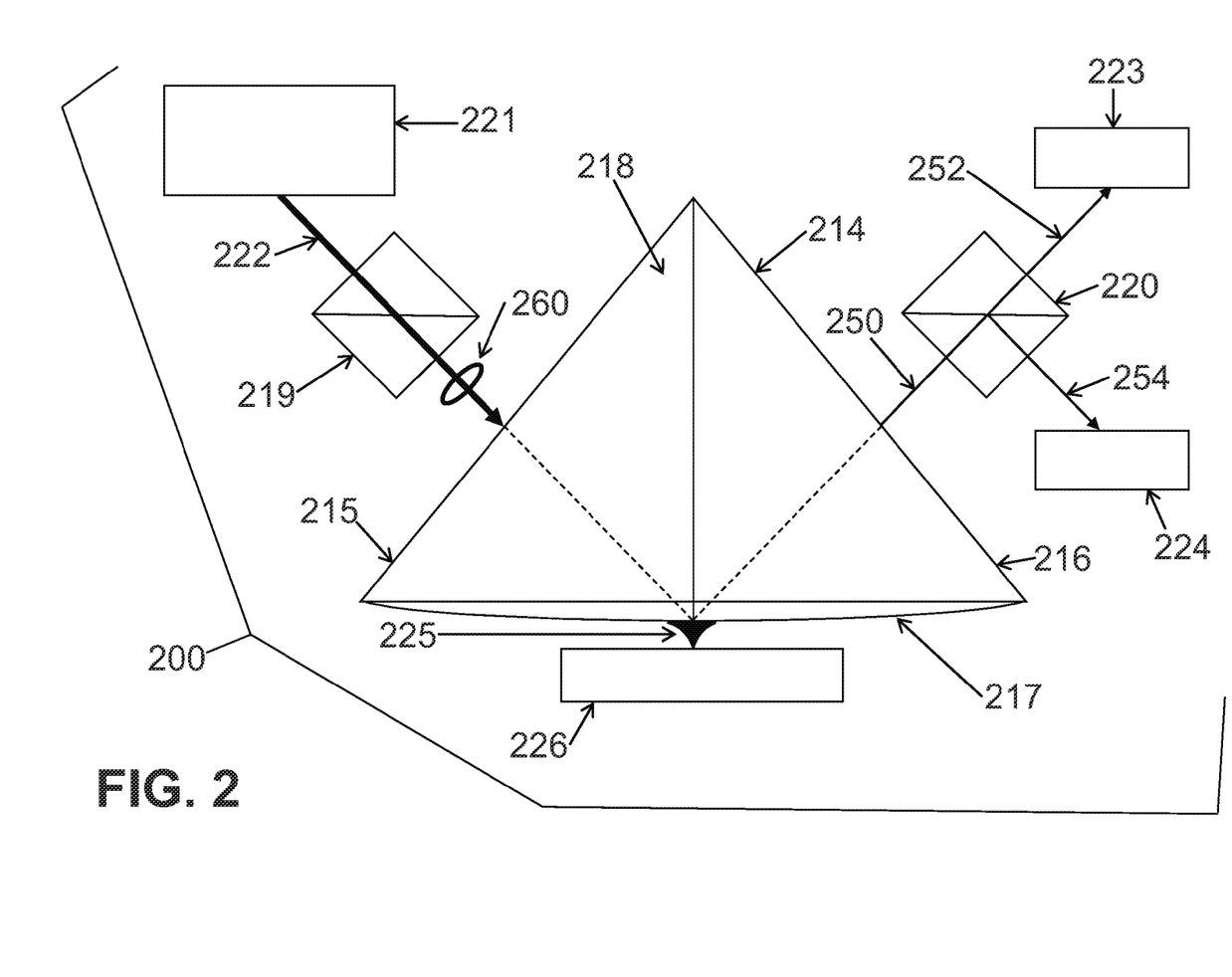
FIG. 2 illustrates a schematic top elevational view of an ellipsometer system in accordance with a second particular embodiment.

FIG. 2 illustrates a schematic top elevational view of ellipsometer system 200 in accordance with preferred second embodiment.

System 200 comprises cavity 214 with a cavity medium 218. Cavity 214 may consist essentially of a single optical element comprising a material with very high internal light transmission. In particular implementations, cavity medium 218 comprises fused silica. Cavity medium 218 comprises surfaces 215 and 216. Surfaces 215 and 216 may comprise high-reflectivity dielectric coatings. In particular implementations one or more of surfaces 215 and 216 may collectively or separately comprise a reflectivity of at least 97%, and preferably at least 99.9%. Cavity medium 218 comprises surface 217 that may be convex, as shown. In particular implementations surface 217 is superpolished (in more particular implementations with a surface roughness less than about 10 nm RMS, and preferably less than about 0.4 nm RMS). Surface 215 is substantially orthogonal to surface 216, as shown. In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, additional cavity elements, cavity medium comprised of material other than fused silica, surface(s) that are highly reflective without a coating, surfaces with different shapes, and/or configurations with reflective surfaces that are not substantially orthogonal.

System 200 comprises polarizer 219 and light source 221, Light source 221 may comprise a diode laser. In an alternate embodiment, light source 221 comprises a pulsed dye laser, Polarizer 219 is interposed between light source 221 and surface 215. In operation, light source 221 generates radiation pulse 222, as shown. System 200 comprises lens 260 selected to traverse mode match radiation pulse 222 to cavity 214, as shown. Radiation pulse 222 passes through lens 260 and polarizer 219 into surface 215. Polarizer 219 polarizes radiation pulse 222 at an angle $\theta_3$ (not shown) to the geometric plane formed by polarizer 219, cavity medium 218, and polarizer 220, as shown. Angle $\theta_3$ is substantially 45° so that radiation pulse 222 comprises nonzero polarization components both parallel and perpendicular to such geometric plane. In particular implementations, the initial phase relation of polarization components is fixed. In particular implementations, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, larger or smaller values for $\theta_1$, multiple light sources, and/or alternate positioning.

Radiation pulse 222 passes through surface 215, and total internal reflection occurs at surface 217, creating evanescent wave 225 decaying exponentially into the region external to cavity medium 218, as shown. Material 226 is placed within the decay length of evanescent wave 225, as shown. System 200 comprises polarizer 220. In operation, radiation pulse 222 reflects off surface 216, the majority of radiation pulse 222 is reflected back toward surface 217, and a small portion of radiation pulse 222, transmitted pulse 250, exits cavity 214 through surface 216 toward polarizer 220, as shown. Polarizer 220 separates transmitted pulse 250 into first polarization component 252 and second polarization component 254 which are substantially orthogonal to each other. Polarizer 220 polarizes transmitted pulse 250 at angle $\theta_4$ (not shown) to the geometric plane of the first and second orthogonally oriented polarization components 252 and 254. In particular implementations, angle $\theta_4$ is 45°. In particular implementations, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, larger or smaller values for $\theta_4$, an arrangement with first polarization component at an angle larger or smaller than orthogonal to second polarization component, utilizing circularly or elliptically polarized light, and/or alternate positioning.

Ellipsometer system 200 comprises detectors 223 and 224, as shown, which each comprises a photomultiplier. Polarizer 220 is interposed between surface 216 and detector 223, as shown. Detector 223 is positioned so that first polarization component 252 is measured. Detector 224 is positioned so that second polarization component 254 is measured. Data collected from detector 223 and detector 224 is used to determine the decay time and the time-dependent polarization of radiation pulse 222. By monitoring the time-dependence of the polarization during the lifetime of radiation pulse 222, the ellipsometric phase shift can be accurately determined from the oscillation frequency of the polarization. The decay time and time-dependent polarization are evaluated to determine properties of material 226. In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, detectors other than photomultipliers, detectors comprising avalanche photodiodes, detectors comprising other photon-counting technologies, and/or alternate positioning.

Cavity losses are minimized through the use of ultra-high transmission optical materials, ultra-high reflectivity coatings, superpolishing, and proper cavity design. In a particular embodiment, detector 223 and detector 224 provide detection data to a digitizing means (not shown, but which may comprise a digital oscilloscope). In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, other means of preventing cavity losses, and/or digitizing means or other digitizers other than a digital oscilloscope.

The decay time $\tau(\omega)$ of the digitized signal may be approximated by:

$$\tau(\omega)=t_r/(2(1-R)+A_{bulk}+A_{surf}+A_{abs})$$

where $t_r$ is the round-trip time in the cavity. For the embodiment shown in FIG. 2, R is the reflectivity of surface 215 and surface 216, $A_{bulk}$ is the bulk attenuation by cavity medium 218, $A_{surf}$ is the surface scattering loss at total internal reflecting surface 217 and $A_{abs}$ is the optical absorption by material 226. All of the loss terms in the decay time formula are known and are constant for a given cavity design except the optical absorption of the absorbing material $A_{abs}$. Therefore, a measurement of the actual photon decay time allows one to obtain the unknown quantity $A_{abs}$.

Use of a single optical element for cavity 214 results in a more rugged cavity as compared to other, multi-element cavities. In addition, use of a single optical element for cavity 214 allows for practical remote positioning of cavity 214 from light source 221 and detector 223 and detector 224 without the burden of aligning plural optical elements. Use of a single optical element for cavity 214 also allows for a smaller, more compact cavity that takes up less space. In alternative implementations, the light source and/or detector(s) may be optically coupled to the optical cavity with fiber optic materials (not shown).

In alternative implementations, a picosecond or femtosecond pulsed laser, preferably with continuum generation, may be used as a light source and frequency analysis of the output signal may be performed either by interferometry or dispersion methods. In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, other types of pulsed lasers, and/or other methods for performing frequency analysis.

State-of-the-art polishing techniques may be utilized to provide a surface quality with a sufficiently high Q-factor, resulting in surfaces with less than 10 nm RMS surface roughness, preferably less than about 0.4 nm RMS. Cavity 214 may form a stable optical resonator, so that an injected light pulse will retrace its path in the cavity a large number of times. The beam waist associated with the stable mode of cavity 214 is located in the vicinity of surface 217 to optimize spatial resolution. Material 226 is probed by radiation pulse 222 a number of times N, equal to the ratio of the decay time to one-half the round trip time. This value will typically be on the order of 1,000.

Figure 3:
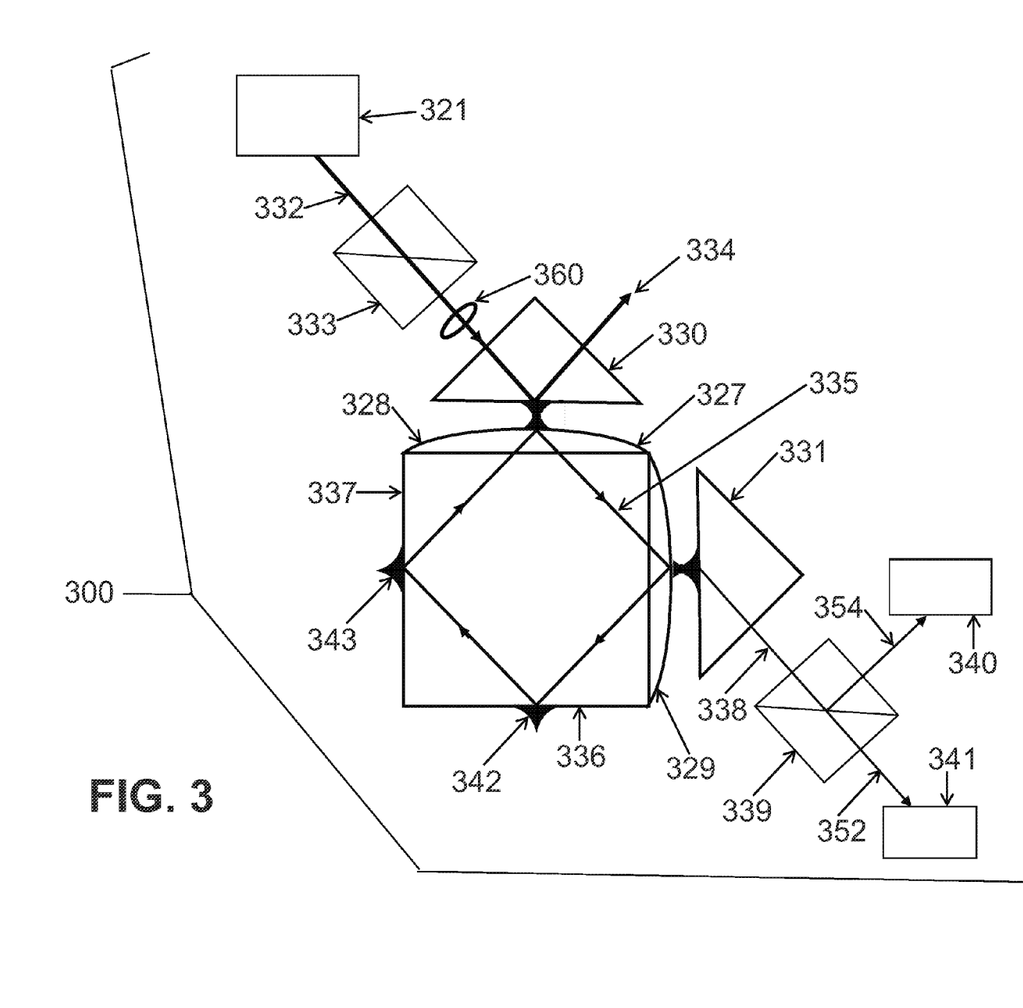
FIG. 3 illustrates a schematic top elevational view of an ellipsometer system in accordance with a third embodiment.

FIG. 3 illustrates a schematic top elevational view of ellipsometer system 300. System 300 comprises cavity 327. Cavity 327 consists essentially of a single optical element and comprises a substantially regular, planar polygon. Cavity 327 comprises planar surfaces and/or convex surfaces. In particular implementations, cavity 327 comprises at least one convex surface arranged so that cavity 327 is stable for internal ray trajectories, as shown. Cavity 327 comprises planar surface 336, planar surface 337, convex surface 328, and convex surface 329. In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, additional optical elements, cavity with shapes other than a regular planar polygon, cavity with more or less planar surfaces, and/or cavity with more or less convex surfaces.

System 300 comprises an input coupler 330. Preferably, input coupler 330 is arranged to allow optical radiation to enter cavity 327, as shown, by a photon tunneling mechanism sometimes referred to as frustrated total reflection (FTR) in IN. Court and F. K. Von Willisen, Appl. Opt. 3, p. 719 (1964) which is incorporated herein by reference. Preferably, input coupler 330 comprises a prism, as shown. The extent of coupling provided by input coupler 330 depends on the distance between input coupler 330 and cavity 327. In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, input coupling means other than a prism, and/or input coupler comprising a cavity element.

System 300 comprises output coupler 331. Output coupler 331 is arranged to allow optical radiation to exit cavity 327 via FTR. In particular implementations, output coupler 331 comprises a prism. The extent of coupling provided by output coupler 331 depends on the distance between output coupler 331 and cavity 327. The choice of radius of curvature for convex surface 328 and surface 329 depends on the size of cavity 327. For example, if the length of planar surface 336 is about 7.5 mm, the length of planar surface 337 is about 7.5 mm, the length of convex surface 328 is about 7.5 mm, and the length of convex surface 329 is about 7.5 mm, then a radius-of-curvature (ROC) for convex surface 328 of about 2.23 cm, and an ROC for convex surface 329 of about 2.23 cm is preferable, System 300 comprises light source 321. Light source 321 may comprise a laser. Polarizer 333 is interposed between light source 321 and input coupler 330, Light source 321, in particular implementations, generates radiation pulse 332. Radiation pulse 332 is directed into polarizer 333, and then into input coupler 330 with an angle of incidence at the base of the input coupler 330 which exceeds the critical angle so that total reflection occurs, producing a reflected pulse 334, as shown. A portion of radiation pulse 332 results in injected radiation pulse 335 within cavity 327 via photon tunneling. System 300 comprises lens 360, selected to traverse mode match radiation pulse 335 to the cavity according to the principals discussed in H. Kogelnik. Bell System Tech, Journal, March 1965, p. 455, which is incorporated herein by reference. Injected radiation pulse 335 is arranged to establish a stable trajectory so as to circulate around cavity 327 and be totally reflected by all encountered planar surfaces (for example, planar surface 336 and planar surface 337) and convex surfaces (for example, convex surface 328 and convex surface 329). The loss per round-trip for the circulating injected radiation pulse 335 is made very small by superpolishing all surfaces (planar surface 336, planar surface 337, convex surface 328 and convex surface 329), and by fabricating cavity 327 from highly transmissive material. For a 0.1 nm RMS surface, effective mirror reflectivities of 99.9999% are possible, allowing injected radiation pulse 335 to circulate in cavity 327 for greater than 100,000 round trips within the pulse decay time.

A small fraction of circulating injected radiation pulse 335 exits cavity 327 via output coupler 331 as output coupled radiation pulse 338. System 300 comprises polarizer 339. Output coupled radiation pulse 338 passes through polarizer 339 which separates radiation pulse 338 into first polarization component 352 and second polarization component 354, as shown. Polarizer 339 separates transmitted output coupled radiation pulse 338 so that first polarization component 352 is substantially orthogonal to second polarization component 354. Polarizer 339 polarizes output coupled radiation pulse 338 at angle $\theta_5$ (not shown) to the geometric plane of the orthogonally oriented first and second polarization components 352 and 354. Preferably, $\theta_5$ is 45°. In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, larger or smaller values for $\theta_5$, an arrangement with first polarization component at an angle larger or smaller than orthogonal to second polarization component, utilizing circularly or elliptically polarized light, and/or alternate positioning.

System 300 comprises detectors 340 and 341, each comprising a photomultiplier. Detector 340 is positioned so that first polarization component 352 is measured. Detector 341 is positioned so that second polarization component 354 is measured. By monitoring output coupled radiation pulse 338 as a function of time over the circulating pulse lifetime, data collected from detector 340 and detector 341 is used to determine a decay curve which is characteristic of the total intrinsic cavity losses for system 300. Material(s) (not shown) may be placed within evanescent wave 342 and/or evanescent wave 343, and the properties of such material(s) may be determined by comparing the change between the intrinsic decay rate of the system when the materials are not present (as shown) to the decay rate with material present. The decay rate with material present will be different because absorption of an evanescent wave by the material will incur additional losses. In particular implementations, for example, spatial constraints, calibration issues, tolerances, materials employed, manufacturing costs, maintenance costs and other factors known to those of ordinary skill in the art, other arrangements may be configured which achieve the functional operation of the presently disclosed systems but which use, for example, detectors other than photomultipliers, detectors comprising avalanche photodiodes, detectors comprising other photon-counting technologies, and/or alternate positioning.

The extent of output coupling is selected to be small to minimize total cavity losses, but large enough so that output coupled radiation pulse 338 has sufficient intensity to permit effective detection by detector 340 and detector 341.

A phase shift, δ, of circulating injected radiation pulse 335 is introduced by the matter within the evanescent wave with every pass within cavity 327. By monitoring the time-dependence of the polarization during the lifetime of injected radiation pulse 335, the ellipsometric phase shift can be accurately determined from the oscillation frequency of the polarization. The wavelength-dependent oscillation frequency of the polarization of the bare cavity, $\omega_c(\lambda)$, is given by:

$$\omega_c(\lambda)=\phi_c(\lambda)/t_r$$

where tr is the round-trip time in the cavity, and $\phi_c(\lambda)$ is the wavelength-dependent total s-p phase shift accumulated over a cavity round trip for the bare cavity. When matter is added into the region of the evanescent wave, there is a shift in the oscillation frequency, $\Delta\omega(\lambda)$, which is given by:

$$\Delta\omega(\lambda)=\delta(\lambda)/t_r$$

where $\delta(\lambda)$ is the wavelength-dependent ellipsometric phase shift introduced by the probed material for a single roundtrip of the cavity, it is the desired quantity to be determined, and is given by $\Delta\omega(\lambda)/t_r$.

The cavity polarization oscillation frequency $\omega_c(\lambda)$ depends on the phase shift $\phi_c(\lambda)$ and the roundtrip time $t_r$. The phase shift $\phi_c(\lambda)$ depends on both the incidence angle, and the refractive indices of the cavity material and that of the material within the evanescent wave. Therefore, the phase shift $\phi_c(\lambda)$ can be controlled in two ways: (a) by varying the incidence angle on the internally reflective surface, as is possible in the setup of FIG. 1; and (b) for the case when the test material is in a solvent at the internally reflective surface, the refractive index of the solvent can be selected to give the desired value of $\phi_c(\lambda)$.

The difference frequency $\Delta\omega(\lambda)$ is usually small compared to $\omega_c(\lambda)$, so that the polarization oscillation frequency of the cavity is well approximated by $\omega_c(\lambda)$, and the oscillation period is $T_p=2\pi/\omega_c(\lambda)$. For this oscillation to be observed, both the injected radiation pulse width and the detector time resolution must be significantly shorter than $2\pi/\omega_c(\lambda)$.

It is instructive to consider two reasonable extremes of the polarization oscillation period. For a large cavity with tr≈6 ns (with a cavity size of about 1 m), and with $\phi_c(\lambda_0)\approx0.4$, the polarization oscillation period is $T_p\approx100$ ns. This oscillation can be observed using commercial nanosecond lasers and detectors (PMTs or photodiodes). For a small cavity with $t_r\approx0.06$ ns cavity size of about 1 cm), and with $\phi_c(\lambda_0)\approx0.4$, then $T_p\approx1$ ns. The observation of this oscillation requires sub-nanosecond timescale radiation pulses and detectors with sub-nanosecond time resolution.

In alternative embodiments (not shown) cavity 327 may comprise a sphere, disc, cylinder, or toroid instead of a substantially regular, planar polygon.

Figure 4:
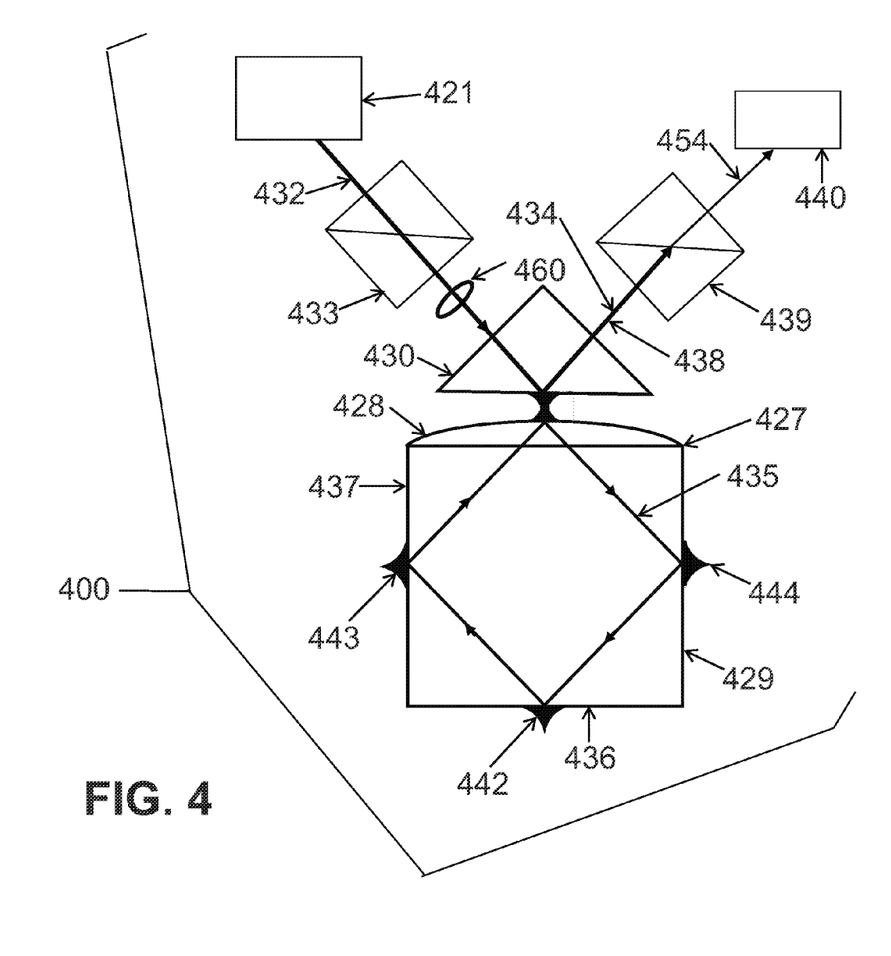
FIG. 4 illustrates a schematic top elevational view of an ellipsometer system in accordance with a fourth embodiment.

FIG. 4 illustrates a schematic top elevational view of ellipsometer system 400. System 400 comprises cavity 427. In particular implementations, cavity 427 comprises at least one convex surface arranged so that cavity 427 is stable for internal ray trajectories, as shown. Cavity 427 comprises planar surface 436, planar surface 437, convex surface 428, and planar surface 429. In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, additional optical elements, cavity with shapes other than a regular planar polygon, cavity with more or less planar surfaces, and/or cavity with more or less convex surfaces.

System 400 comprises coupler 430. Coupler 430 is arranged to allow optical radiation to enter cavity 427, as shown, by a photon tunneling mechanism. Coupler 430 may comprise a prism. In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, coupling means other than a prism, and/or coupler comprising a cavity element. Coupler 430 is arranged to allow optical radiation to exit cavity 427 via photon tunneling, as shown.

System 400 comprises light source 421. Light source 421 may comprise a laser. Polarizer 433 is interposed between light source 421 and coupler 430. Light source 421 generates radiation pulse 432. Radiation pulse 432 is directed into polarizer 433, and then into coupler 430 with an angle of incidence at the base of coupler 430 which exceeds the critical angle so that total reflection occurs, producing a reflected pulse 434, as shown. A portion of radiation pulse 432 results in injected radiation pulse 435 within cavity 427 via photon tunneling, as shown. System 400 comprises lens 460 selected to traverse mode match radiation pulse 435 to the cavity. Injected radiation pulse 435 is arranged to establish a stable trajectory so as to circulate around cavity 427 and be totally reflected by all encountered planar surfaces and convex surfaces, as shown. Material(s) (not shown) may be placed within evanescent wave 442 and/or evanescent stave 443 and/or evanescent stave 444, and the properties of such material(s) may be determined as described herein.

Coupler 430 functions as both input coupler and output coupler. A small fraction of circulating injected radiation pulse 435 exits cavity 427 via coupler 430 as output coupled radiation pulse 438. Polarizer 439, and detector 440 are positioned to receive the output coupled radiation pulse 438 coincident with radiation pulse 434. Output coupled pulse 438 and the coincident radiation pulse 434 are separated by polarizer 439, as shown. Polarization orientation for polarizer 439 is orthogonal to polarization orientation of polarizer 433, so that output coupled radiation pulse 438 is separated from radiation pulse 434. The only light that passes through polarizer 439 is light which has experienced a phase shift between polarization components that are neither parallel nor perpendicular to the polarizer axis. As before, the reflective surfaces in the cavity provide such a phase shift. By monitoring the time-dependence of the polarization during the lifetime of radiation pulse 434, the ellipsometric phase shift can be accurately determined from the oscillation frequency of the polarization. Output coupled radiation pulse 438 is detected by detector 440. One advantage of this embodiment is that both input and output coupling is achieved with a single optical element.

In alternate implementations (not shown) cavity 42.7 may comprises a sphere, disc, cylinder, or torpid instead of a substantially regular, planar polygon.

Figure 5:
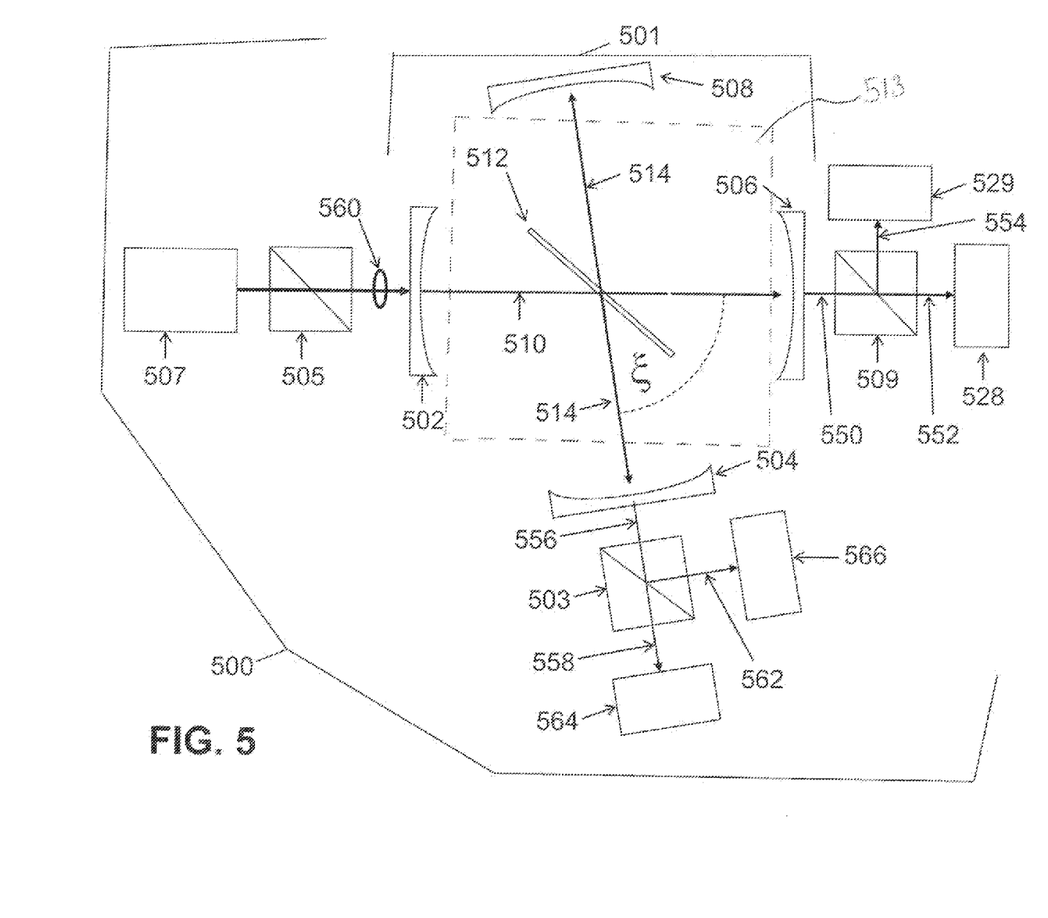
FIG. 5 illustrates a schematic top elevational view of an ellipsometer system in accordance with a fifth embodiment.

In principle, for the embodiments shown in FIG. 1. FIG. 2. FIG. 3. FIG. 4 and FIG. 5, all the phase information is contained in the signal from one of the two detectors (for example, one of the detectors from the pairs detector 108 or detector 109, detector 223 or detector 224, and detector 340 or detector 341). The signal from the detector that detects the parallel component, $S_\parallel$, (for example detector 108, detector 223, and detector 341) will be of the form:

$$S_\parallel = A(t)\cos^2\omega_c(\lambda)t + B(t)$$

where A(t) is the envelope of the polarization oscillation signal, which under ideal conditions is well-approximated by the exponential decay $e^{-t/\tau(\omega)}$. The signal from the detector that detects the perpendicular component, $S_\perp$, (for example detector 109, detector 224, and detector 340) will be of the form:

$$S_\perp = A(t)\sin^2\omega_c(\lambda)t + B(t)$$

If the experiment is working ideally, then the form of the envelope A(t) will indeed be well described by $e^{-t/\tau(\omega)}$ so then the frequency of the polarization oscillation can be determined from the oscillation in the signal from either detector ($\cos^2\omega_c(\lambda)t$ for one detector, and $\sin^2\omega_c(\lambda)t$ for the other).

However, there are many experimental factors and uncertainties that can alter the form of the oscillation envelope (these include, hut are not limited to, poor optical alignment, cavity mode beating, and non-linearity of the detector response to the signal intensity). In such cases, the signal from both detectors provides a robust method of eliminating these sources of error. For example, in the ratio of the two detector signals, if B(t) is negligible, the polarization oscillation envelope A(t) cancels (as it is common to both), and the ratio is equal to $\tan^2\omega_c(\lambda)t$, from which $\omega_c(\lambda)$ can be determined directly. Otherwise, if B(t) is not negligible, the difference of the two detector signals will be of the form:

$$(S_\parallel - S_\perp) = A(t)\cos2\omega_c(\lambda)t$$

From which $\omega_c(\lambda)$ can be determined, such as from the Fourier transform of this signal.

In particular implementations, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, radiation pulses having either a narrow or broad spectrum. For example, from a narrow bandwidth of less than about 1 nm, to an intermediate bandwidth of about 40 nm (such as, for example, are typical for a femtosecond laser), to a much broader spectrum, including "white light". In the case of broader spectrum radiation pulses, the output light can be spectrum analyzed with a prism or grating, and the spectrum can be analyzed for the ellipsometric parameters, as a function of wavelength.

FIG. 5 illustrates a schematic top elevational view of ellipsometer system 500. Ellipsometer system 500 comprises optical cavity 501. Optical cavity 501 comprises four reflectors 502, 504, 506 and 508. In particular implementations, considering issues such as, for example, spatial constraints, tolerances, calibration issues, materials employed, manufacturing costs, maintenance costs, and other factors known to those of ordinary skill in the art, other arrangements may be configured which achieve the functional operation of the presently disclosed systems but which use, for example, a different number of elements, a different element configuration, and/or replacement of a reflector with something functionally similar to a reflector.

In the example provided, reflectors 502, 504, 506 and 508 are highly-reflective. Reflectors 502, 504, 506 and 508, for example, comprise a reflectivity of at least 97%, and preferably at least 99.9%. Reflectors 502, 504, 506 and 508 are concave, as shown, with approximately equal radii or curvature. In particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, a reflectivity less than 97%, non-concave reflectors, and/or reflectors of unequal radii.

Ellipsometer system 500 comprises light source 507, as shown (at least embodying herein a light-generating means for generating at least one laser pulse). Ellipsometer system 500 comprises polarizer 505 (at least embodying herein a first-polarizing means for polarizing at least a portion of such at least one first light pulse into at least one first polarized light pulse). Ellipsometer system 500 also comprises at least one other polarizer 503 and 509. Polarizer 505, for this embodiment, is interposed between light source 507 and reflector 502. In operation, light source 507 generates a radiation pulse 510. Ellipsometer system 500 comprises lens 560 selected to traverse mode match radiation pulse 510 to cavity 501. Radiation pulse 510 passes through lens 560 and polarizer 505 into cavity 501. Polarizer 505 polarizes radiation pulse 510 at an angle $\theta_1$ (not shown) to the geometric plane 513 illustrated by the plane of the paper FIG. 5 is printed on, formed by the travel path of the radiation pulse 510 and 514 between reflectors 502, 504, 506 and 508. Angle $\theta_1$, in particular implementations, is substantially 45° so that radiation pulse 510 comprises non-zero polarization components both parallel and perpendicular to such geometric plane 513. In particular implementations, the initial phase relation of polarization components is fixed. In particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, larger or smaller values for $\theta_1$, multiple light sources, and/or alternate positioning.

Reflectors 502 and 506 are aligned with each other and Reflectors 504 and 508 are aligned with each other with an angle between the aligned paths between them, as shown. This configuration is particularly useful in the semiconductor industry, but may be used in general for any non-absorbing or weakly absorbing wafer, window, or slide, that both reflects and transmits incident light. For a particular non-limiting example using a silicon wafer, a silicon wafer 512 is placed within the cavity 501, which both reflects and transmits the incoming radiation pulse 510 to produce reflected light pulses 514. Radiation pulse 510 reflects off reflector 506, the majority of radiation pulse 510 is reflected back toward the silicon wafer 512, and a small portion of radiation pulse 510, transmitted pulse 550, is transmitted through reflector 506 toward polarizer 109, as shown. For use with silicon wafers, it is anticipated that the radiation pulse 510 will have a wavelength between 1.5 and 3 micrometers, where silicon does not absorb strongly, so that the light pulse is mostly only transmitted or reflected. Because of the reflectors 502, 504, 506 and 508, however, whether transmitted or reflected, the radiation pulse 510 and its counterparts remain almost entirely within the cavity 501.

Polarizer 509 separates transmitted pulse 550 into first polarization component 552 and second polarization component 554, as shown (at least embodying herein second polarizing means for polarizing at least a portion of such at least one first polarized light pulse into at least one second polarized light pulse and for polarizing at least a portion of such at least one first polarized light pulse into at least one third polarized light pulse). Polarizer 509 separates transmitted pulse 550 so that first polarization component 552 is substantially orthogonal to second polarization component 554 and polarizes transmitted pulse 550 at angle $\theta_2$ (not shown) to the geometric plane formed by the first and second polarization components 552 and 554 orthogonal to each other. Angle $\theta_2$ may be substantially 45°. In particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, larger or smaller values for $\theta_2$, an arrangement with first polarization component at an angle larger or smaller than orthogonal to second polarization component, utilizing circularly or elliptically polarized light, and/or alternate positioning.

Ellipsometer system 500 comprises detectors 528 (at least embodying herein first-detector means for detecting such at least one second polarized light pulse) and 529 (at least embodying herein second-detector means for detecting such at least one third polarized light pulse), Detectors 528 and 529 may each comprise a photomultiplier. Detector 528 is positioned so that a first polarization component 552 is measured and detector 529 is positioned so that second polarization component 554 is measured, as shown, Data collected from detector 528 and detector 529 is used to determine decay time of radiation pulse 510 and to determine time-dependent polarization of the radiation pulse 510. By monitoring the time-dependence of the polarization during the lifetime of radiation pulse 510, the ellipsometric phase shift can be accurately determined from the oscillation frequency of the polarization. Such decay time and time-dependent polarization are evaluated to determine properties of the material of the silicon wafer 512, in particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, detectors other than photomultipliers, detectors comprising avalanche photodiodes, detectors comprising other photon-counting technologies, alternate positioning, and/or utilizing only one detector instead of two detectors (or more) to determine decay time and/or time-dependent polarization, Reflected radiation pulse 514 reflects off reflectors 504 and 508, the majority of reflected radiation pulses 514 are reflected back toward the silicon wafer 512, A small portion of reflected radiation pulse 514, transmitted pulse 556, is transmitted through reflector 506 toward polarizer 503, as shown. Polarizer 503 separates transmitted pulse 556 into first polarization component 558 and second polarization component 562, as shown (at least embodying herein second polarizing means for polarizing at least a portion of such at least one first polarized light pulse into at least one second polarized light pulse and for polarizing at least a portion of such at least one first polarized light pulse into at least one third polarized light pulse). Polarizer 503 separates transmitted pulse 556 so that first polarization component 558 is substantially orthogonal to second polarization component 562 and polarizes transmitted pulse 556 at angle $\theta_2$ (not shown) to the geometric plane formed by the first and second polarization components 558 and 562 orthogonal to each other. Angle $\theta_3$ may be substantially 45°. In particular implementations, considering issues such as, for example, spatial constraints, calibration issues, tolerances, materials employed, manufacturing costs, maintenance costs, and other factors known to those of ordinary skill in the art, other arrangements may be configured which achieve the functional operation of the presently disclosed systems but which use, for example, larger or smaller values for $\theta_3$, an arrangement with first polarization component at an angle larger or smaller than orthogonal to second polarization component, utilizing circularly or elliptically polarized light, and/or alternate positioning.

Although the particular implementation illustrated in FIG. 5 includes a first set including a polarizer 503 and detectors 564 and 566, and a second set including a polarizer 509 and detectors 528 and 529, only one set is needed to accurately determine the properties of the silicon wafer material. In particular implementations either the first or second sets may be removed as redundant, Additionally, although the particular implementation illustrated in FIG. 5 uses four reflectors 502, 504, 506 and 508, in an alternate, simpler embodiment where the wafer 512 is highly reflecting (i.e. R>0.99, which can be achieved for silicon by making the angle ξ in FIG. 5 very small on the order of about 1°), then the process can be performed with only two reflectors 502 and 504 and the remaining components of the system associated with the other two reflectors 506 and 508 are not needed.

In FIG. 5, the path length from the wafer 512 to the reflectors 504 and 508 introduces a phase shift compared to the path length on the other arm of the cavity between reflectors 502 and 506. For particular embodiments, it may be convenient to control the distance from the wafer 512 to the reflectors 504 and 508 using motor controls coupled to the reflectors, such as piezoelectric motors with subnanometer precision to enable adjustments in the distances between the wafer 512 and the reflectors 504 and 508.

Figure 6:
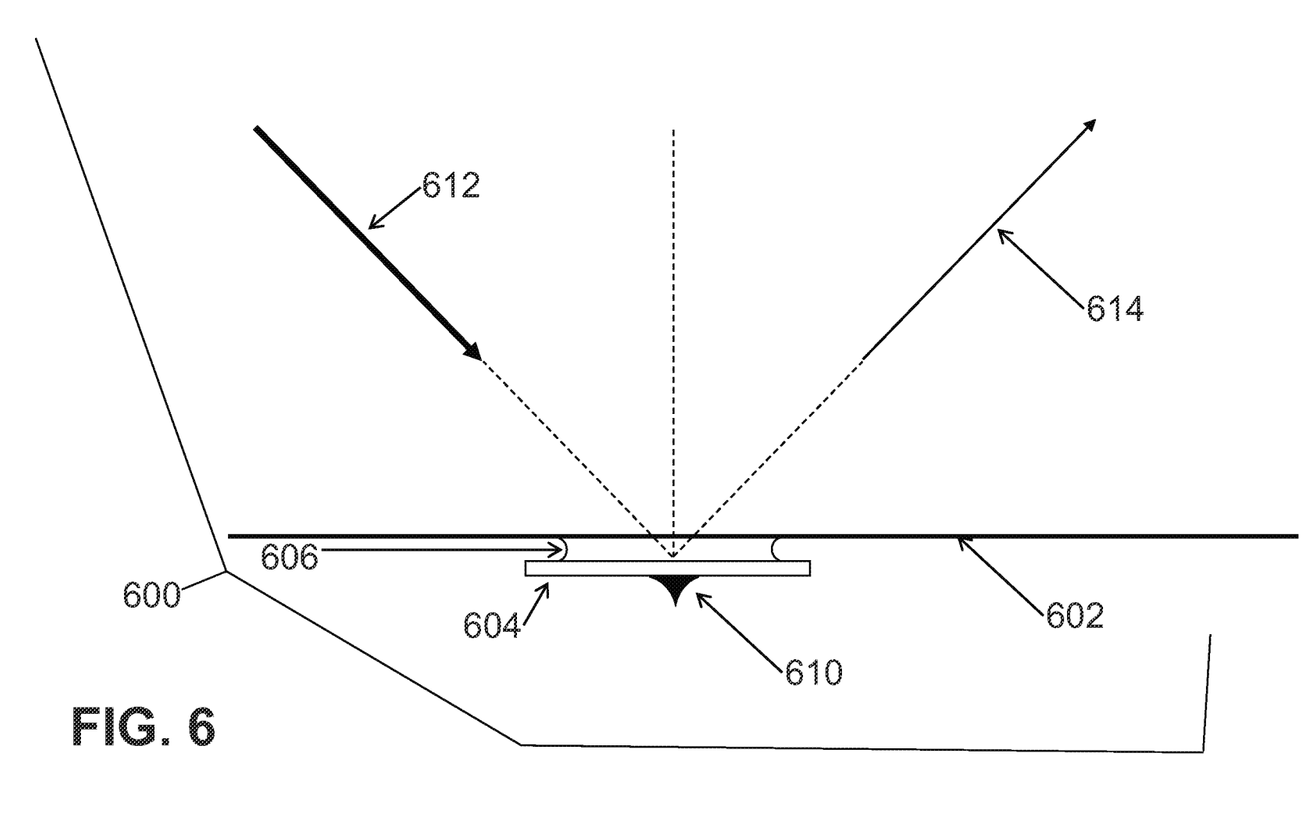
FIG. 6 illustrates a schematic top devotional view of an ellipsometer system in accordance with a sixth embodiment.

FIG. 6 illustrates a schematic top elevational view of a portion 600 of an ellipsometer system in accordance with a sixth embodiment. In particular embodiments of this disclosure where a prism is used (see, e.g. FIGS. 1-4), a prism cover slip 602 may be used as a protection to the prism 604. For the remainder of the ellipsometer system not shown), it may be configured according to one or more of the previous embodiments using a prism. For the portion 600 of the system shown, a prism cover slip 602 may comprise a disposable cover slip 602 formed of a material having the same index of refraction as the prism 604 (for example, by forming them of the same material, such as fused silica). A fluid 606, having an index of refraction matched to the cover slip 602 and prism 604 may be used. By using a protective cover slip 602 and fluid 606 over the prism 604 within the cavity, if needed the cover slip 602 may be replaced without affecting the prism 604 or the need to realign the cavity. Because the indices of refraction for each of the cover slip 602, the fluid 606 and the prism 604 is the same, the operation and refraction of the light incident on the cover slip 602, fluid 606 and prism 604 combination is the same as the prism 604 without the cover slip 602 and fluid 606. Such operation and refraction, including the evanescent-wave 610, an incoming light pulse 612 (polarized or not) and a polarized light pulse 614, has been described in relation to each of the previous embodiments including a prism. Those of ordinary skill in the art will readily understand how to include a cover slip 602 and fluid 606 in each of those embodiments from this disclosure. Although applicant has described applicant's preferred embodiments, it will be understood that the broadest scope of this invention includes such modifications as diverse shapes and sizes and materials, etc. Such scope is determined only by the below claims as read in connection with the above specification. Further, many other advantages will now be apparent to those skilled in the art from the above descriptions and the below claims.

In particular implementations and embodiments of the intra-cavity ellipsometer systems illustrated and described herein, the sensitivity of the measurements of material characteristics and properties to changes in decay time $\tau(\omega)$ or changes in phase shift $\delta(\omega)$, can be amplified by applying optical coatings on the reflecting surface of the material being tested or at the reflecting surface of a prism used in an embodiment, or even on a cover slip for a prism. In particular implementations, these thin coatings may be made of metal, such as gold or silver as is used in the technique of Surface Plasmon Resonance, or specifically tailored multi--layer dielectric coatings. It has been found that using highly reflective dielectric coated mirrors (optimized for high reflectivity) as the reflective surface for the placement of the material being tested, the sensitivity of the phase shift measurements can be increased by a factor of at least 100. The specific optimal multi-layer dielectric coatings for the reflecting surface of the prisms or the cover slip will vary depending on the particular implementation and material being tested. Those of ordinary skill in the art will readily be able to determine an appropriate dielectric optical layer materials and appropriate optimized thickness for the particular implementation (designed using similar optimization procedures as those used to design highly reflective, multi-layer, dielectric mirrors).

The materials used for implementations of ellipsometer systems like those disclosed in this document may be made of conventional materials used to make goods similar to these in the art, such as, by non-limiting example, plastics, glass, metals, semiconductors, composites, and the like. Many different forms of radiant light pulses or other light injecting means may be used as well and this disclosure is not intended to be limited to the specific examples provided above. For example, any laser such as, by non-limiting example, diode pumped solid state lasers, supercontinuum lasers, pulsed dye lasers, picoseconds lasers, femtosecond pulsed laser, continuous wave laser and diode lasers are all specifically contemplated. Those of ordinary skill in the art will readily he able to select appropriate materials and manufacture these products from the disclosures provided herein.

The implementations listed here, and many others, will become readily apparent from this disclosure. From this, those of ordinary skill in the art will readily understand the versatility with which this disclosure may be applied.

The invention claimed is:

1. An ellipsometric system comprising:
   at least one light source structured and arranged to generate at least one first light pulse;
   at least one first-polarizer structured and arranged to polarize at least a portion of such at least one first light pulse into at least one first polarized light pulse;
   at least one closed stable optical cavity structured and arranged to generate a measurable ellipsometric phase shift in the at least one first polarized light pulse;
   at least one first light-detector;
   at least one second-polarizer structured and arranged to polarize at least a portion of such at least one first polarized light pulse into at least one second polarized light pulse and to polarize at least a portion of such at least one first polarized light pulse into at least one third polarized light pulse; and
   at least one second light-detector structured and arranged to detect such at least one third polarized light pulse;
   wherein the at least one first light-detector is structured and arranged to detect such at least one second polarized light pulse.

2. The ellipsometric system according to claim 1 wherein the at least one second-polarizer is structured and arranged so that such at least one third polarized light pulse is substantially orthogonal to such at least one second polarized light pulse.

3. The ellipsometric system according to claim 1 wherein the at least one first-polarizer is structured and arranged to polarize such at least one first polarized light pulse so that such at least one first polarized light pulse comprises non-zero polarization components both parallel and perpendicular to a first geometric plane.

4. The ellipsometric system according to claim 3 wherein the at least one second-polarizer is structured and arranged to polarize such at least one first polarized light pulse at an angle about forty-five degrees from such first geometric plane.

5. The ellipsometric system according to claim 1 wherein the at least one first-polarizer and the at least one second-polarizer are combined in one unitary element.

6. The ellipsometric system according to claim 1 wherein:
the light source comprises at least one laser;
the at least one closed stable optical cavity comprises at least one first reflector; and
the at least one closed stable optical cavity comprises at least one second reflector.

7. The ellipsometric system according to claim 6 wherein a distance between a material within the closed optic cavity and at least one of the at least one first reflector and the at least one second reflector is controlled by at least one piezoelectric motor coupled to the respective at least one first reflector or the at least one second reflector.

8. The ellipsometric system according to claim 1 wherein:
the at least one closed stable optical cavity comprises at least one prism;
the at least one first reflector comprises at least one first concave reflecting portion; and
the at least one second reflector comprises at least one second concave reflecting portion.

9. The ellipsometric system according to claim 1 wherein:
the at least one first light-detector comprises at least one first photomultiplier; and
the at least one second-detector comprises at least one second photomultiplier.

10. The ellipsometric system according to claim 1 wherein:
the light source comprises at least one laser;
the at least one closed stable optical cavity comprises at least one prism;
the at least one prism comprises fused silica;
the at least one closed stable optical cavity further comprises at least one first reflector;
the at least one first reflector comprises at least one first concave reflecting portion;
the at least one closed stable optical cavity further comprises at least one second reflector;
the at least one second reflector comprises at least one second concave reflecting portion;
the at least one first concave reflecting portion comprises at least one first radius;
the at least one second concave reflecting portion comprises at least one second radius;
the at least one first radius is substantially equal to the at least one second radius;
the at least one first light-detector comprises at least one first photomultiplier; and
the at least one second-detector comprises at least one second photomultiplier.

11. The ellipsometric system according to claim 1 wherein:
the at least one closed stable optical cavity consists essentially of a unitary optical element;
the unitary optical element comprises at least one convex surface; and
the unitary optical element is structured and arranged to provide total internal reflection of such first polarized light pulse.

12. The ellipsometric system according to claim 11 wherein:
the at least one unitary optical element comprises at least one first substantially planar surface structured and arranged so that such at least a portion of such at least one first polarized light pulse enters the at least one unitary optical element; and
the at least one unitary optical element comprises at least one second substantially planar surface structured and arranged so that at least a portion of such at least one first polarized light pulse exits the at least one unitary optical element.

13. The ellipsometric system according to claim 12 wherein:
the at least one first substantially planar surface comprises at least one first high-reflectivity coating structured and arranged to internally reflect at least 97% of such at least one first polarized light pulse;
the at least one second substantially planar surface comprises at least one second high-reflectivity coating structured and arranged to internally reflect at least 97% of such at least one first polarized light pulse; and
the at least one convex surface comprises a surface roughness less than 10 nm RMS.

14. The ellipsometric system according to claim 12 wherein:
the at least one first substantially planar surface comprises at least one first high-reflectivity coating structured and arranged to internally reflect at least 99.9% of such at least one first polarized light pulse;
the at least one second substantially planar surface comprises at least one second high-reflectivity coating structured and arranged to internally reflect at least 99.9% of such at least one first polarized light pulse; and
the at least one convex surface comprises a surface roughness less than 0.5 nm RMS.

15. The ellipsometric system according to claim 1 further comprising at least one lens structured and arranged to transverse mode match such at least one first polarized light pulse for the at least one closed stable optical cavity.

16. The ellipsometric system according to claim 1 wherein the at least one closed stable optical cavity comprises at least one substantially regular, substantially planar polygon.

17. The ellipsometric system according to claim 1 further comprising:
at least one input element structured and arranged so that at least a portion of such at least one first polarized light pulse enters the at least one closed stable optical cavity.

18. The ellipsometric system according to claim 17 wherein the at least one input element comprises at least one prism.

19. The ellipsometric system according to claim 17 wherein the at least one input element allows a portion of such at least one first polarized light pulse to enter the at least one closed stable optical cavity via frustrated total reflection photon tunneling.

20. The ellipsometric system according to claim 17 further comprising at least one output element structured and arranged so that at least a portion of such at least one first polarized light pulse exits the at least one closed stable optical cavity.

21. The ellipsometric system according to claim 20 wherein the at least one output element allows a portion of such at least one first polarized light pulse to exit the at least one closed stable optical cavity via frustrated total reflection photon tunneling.

22. The ellipsometric system according to claim 1 wherein the at least one light source is selected from the group consisting of picosecond pulsed laser, femtosecond pulsed laser, diode laser, pulsed dye laser, and continuous wave laser.

23. The ellipsometric system according to claim 1 wherein:
the at least one first light-detector comprises at least one first photodiode; and
the at least one second light-detector comprises at least one second photodiode.

24. The ellipsometric system according to claim 1, wherein the at least one closed stable optical cavity is further structured and arranged to generate at least one evanescent wave from at least a portion of the at least one first polarized light pulse.

25. A method of measuring the ellipsometric angle $\delta$ of a test material, the method comprising the steps of:
- generating at least one first light pulse;
- polarizing the at least one first light pulse into at least one first polarized light pulse;
- injecting the at least one first polarized light pulse into at least one closed stable optical cavity so that test material situated to interact with the at least one first polarized light pulse, will partially absorb the at least one first polarized light pulse;
- polarizing at least a portion of the at least one first polarized light pulse that has exited the at least one closed stable optical cavity, into at least one second polarized light pulse;
- detecting the at least one second polarized light pulse; and
- calculating the ellipsometric angle $\delta$ of the test material from the detected second polarized light pulse.

26. The method of measuring the ellipsometric angle $\delta$ of the test material of claim 25 wherein injecting the at least one first polarized light pulse comprises injecting the at least one first polarized light pulse so that the first polarized light pulse generates at least one evanescent wave, and interacting the test material with the at least one evanescent wave so that the test material partially absorbs the at least one evanescent wave.

* * * * *